US012667632B2

(12) United States Patent
Douglas et al.

(10) Patent No.: US 12,667,632 B2
(45) Date of Patent: Jun. 30, 2026

(54) SYSTEMS AND METHODS TO MITIGATE INFECTION RISK USING FAR UV-C

(71) Applicant: Tyco Fire & Security GmbH, Schaffhausen (CH)

(72) Inventors: Jonathan D. Douglas, Mequon, WI (US); Brennan H. Fentzlaff, Oconomowoc, WI (US); Bernard P. Clement, Mequon, WI (US); Christopher C. Duncan, Milwaukee, WI (US); Charles Gans, Milwaukee, WI (US); Matthew J. Deloge, Milwaukee, WI (US); Tyler A. Smith, Franklin, TN (US)

(73) Assignee: TYCO FIRE & SECURITY GMBH, Neuhausen am Rheinfall (CH)

( * ) Notice: Subject to any disclaimer, the term of this patent is extended or adjusted under 35 U.S.C. 154(b) by 288 days.

(21) Appl. No.: 18/393,257

(22) Filed: Dec. 21, 2023

(65) Prior Publication Data

US 2024/0207468 A1     Jun. 27, 2024

Related U.S. Application Data

(60) Provisional application No. 63/435,194, filed on Dec. 23, 2022.

(51) Int. Cl.
A61L 2/10        (2026.01)
A61L 2/24        (2006.01)
A61L 103/75        (2026.01)

(52) U.S. Cl.
CPC .................. A61L 2/10 (2013.01); A61L 2/24 (2013.01); *A61L 2103/75* (2026.01); *A61L 2202/11* (2013.01); *A61L 2202/14* (2013.01)

(58) Field of Classification Search
CPC .......... A61L 2/10; A61L 2/24; A61L 2103/75; A61L 2202/11; A61L 2202/14
See application file for complete search history.

(56) References Cited

U.S. PATENT DOCUMENTS

| | | |
|---|---|---|
| 8,975,605 B2 | 3/2015 | Neister |
| 9,700,642 B2 | 7/2017 | Neister |

(Continued)

FOREIGN PATENT DOCUMENTS

| | | |
|---|---|---|
| WO | WO-2021/239993 A1 | 12/2021 |
| WO | WO-2022/139887 A1 | 6/2022 |

(Continued)

OTHER PUBLICATIONS

Alvarado et al., "A Methodology to Monitor Airborne PM10 Dust Particles Using a Small Unmanned Aerial Vehicle," Sensors, 2017, vol. 17 (25 pages).

*Primary Examiner* — Nicole M Ippolito
(74) *Attorney, Agent, or Firm* — Foley & Lardner LLP

(57) ABSTRACT

A disinfection device system of a building comprising: a controller comprising at least one processor and at least one memory having instructions stored thereon that, when executed by the at least one processor, are configured to cause the at least one processor to: monitor one or more conditions of a space in the building; and selectively activate and deactivate at least one Far UV-C disinfection device installed in the space using the conditions of the space and one or more of an energy budget, a target total operating cost, or a net emissions target, wherein the Far UV-C disinfection device comprises at least one Far UV-C light source structured to output disinfecting light at a wavelength between 200 nm and 230 nm.

20 Claims, 3 Drawing Sheets

(56)        References Cited

U.S. PATENT DOCUMENTS

| | | | |
|---|---|---|---|
| 10,780,189 | B2 | 9/2020 | Randers-Pehrson et al. |
| 11,007,291 | B2 | 5/2021 | Randers-Pehrson et al. |
| 11,167,051 | B2 | 11/2021 | Randers-Pehrson et al. |
| 11,291,738 | B2 | 4/2022 | Randers-Pehrson et al. |
| 11,357,879 | B2 | 6/2022 | Baxter et al. |
| 11,696,971 | B1 | 7/2023 | Martinez Openiano |
| 11,896,726 | B1 * | 2/2024 | Deshler .................... A61L 2/10 |
| 2015/0316907 | A1 | 11/2015 | Elbsat et al. |
| 2020/0306397 | A1 | 10/2020 | Randers-Pehrson et al. |
| 2021/0318008 | A1 * | 10/2021 | Szoradi ................... F24F 11/56 |
| 2022/0054686 | A1 | 2/2022 | Baxter et al. |
| 2022/0143232 | A1 | 5/2022 | Neister |
| 2022/0203287 | A1 | 6/2022 | Wenger et al. |
| 2022/0203288 | A1 | 6/2022 | Wenger et al. |
| 2022/0205962 | A1 | 6/2022 | Vanderkoy |
| 2022/0207215 | A1 | 6/2022 | Liu et al. |
| 2022/0221184 | A1 | 7/2022 | Gupta et al. |
| 2022/0228756 | A1 | 7/2022 | Gupta et al. |
| 2022/0254483 | A1 | 8/2022 | Boisvert et al. |
| 2022/0277851 | A1 | 9/2022 | Wellig |
| 2022/0282886 | A1 | 9/2022 | Hriljac et al. |
| 2022/0293261 | A1 | 9/2022 | Mcbrady et al. |
| 2022/0305438 | A1 | 9/2022 | Wenger et al. |
| 2022/0305881 | A1 | 9/2022 | Neu et al. |
| 2023/0218791 | A1 * | 7/2023 | Prohaska .................. A61L 2/10 250/454.11 |
| 2023/0343470 | A1 | 10/2023 | Yencho |
| 2024/0181109 | A1 * | 6/2024 | Slycke ..................... A61L 2/24 |

FOREIGN PATENT DOCUMENTS

| | | |
|---|---|---|
| WO | WO-2022/235439 A1 | 11/2022 |
| WO | WO-2022/265815 A1 | 12/2022 |
| WO | WO-2023/141304 A2 | 7/2023 |

* cited by examiner

SYSTEMS AND METHODS TO MITIGATE INFECTION RISK USING FAR UV-C

CROSS-REFERENCE TO RELATED APPLICATIONS AND CLAIM OF PRIORITY

This application claims priority to and the benefit of U.S. Provisional Application No. 63/435,194, filed Dec. 23, 2022, which is incorporated herein by reference in its entirety.

BACKGROUND

The present disclosure relates generally to systems and methods for improving health in a building using occupant-safe disinfectant lighting. The present disclosure relates more particularly to a disinfection tool for mitigating/controlling infection risk using Far UV-C spectrum lighting which is known to be non-toxic for humans at certain dosages.

Maintaining disinfection, or mitigating infection risk, in a building may involve operating building equipment (e.g., UV lighting and/or HVAC systems) to improve health outcomes. In some systems, the building equipment is only capable of maintaining disinfection in part of a building, leaving other areas, often occupied areas, at an elevated infection risk. In some systems, the disinfection devices (e.g. UV lighting) are not safe to expose occupants to, and therefore air and surfaces in occupied zones are not actively disinfected. Maintaining disinfection can be expensive if not performed correctly, and infection of building occupants can also incur significant expenses. Thus, systems and methods are needed to improve building health and maintain sufficient disinfection throughout a building, particularly in occupied areas, while reducing expenses related to maintaining disinfection.

SUMMARY

In one aspect, the present disclosure provides a disinfection device system of a building comprising: a controller comprising at least one processor and at least one memory having instructions stored thereon that, when executed by the at least one processor, are configured to cause the at least one processor to: monitor one or more conditions of a space in the building; and selectively activate and deactivate at least one Far UV-C disinfection device installed in the space using the conditions of the space and one or more of an energy budget, a target total operating cost, or a net emissions target, wherein the Far UV-C disinfection device comprises at least one Far UV-C light source structured to output disinfecting light at a wavelength between 200 nm and 230 nm.

In some embodiments, the at least one processor is configured to selectively activate and deactivate the at least one Far UV-C disinfection device to not exceed one or more of the energy budget, the target total operating cost, or the net emissions target.

In some embodiments, the at least one processor is configured to selectively activate and deactivate the at least one Far UV-C disinfection device to achieve a desired disinfection level, and wherein the at least one processor is configured to allow Far UV-C disinfection device activation to exceed one or more of the energy budget, the target total operating cost, or the net emissions target to achieve the desired disinfection level.

In some embodiments, an Equivalent Clean Airflow for infection mitigation of the Far UV-C disinfection device is stored in the controller.

In some embodiments, the controller selectively activates and deactivates the Far UV-C disinfection device to meet an infection risk mitigation standard.

In some embodiments, the system further comprises a Far UV-C tracer, wherein the Far UV-C tracer is used to measure an effective disinfection provided by the Far UV-C disinfection device in the building and the effective disinfection is stored in the controller.

In some embodiments, the controller periodically triggers a new Far UV-C tracer test to measure the effective disinfection provided by the Far UV-C disinfection device.

In some embodiments, the controller is configured to use the effective disinfection of the one or more disinfection devices to trigger a replacement of the one or more disinfection devices when the effective disinfection falls below a pre-determined threshold.

In some embodiments, the disinfection device further comprises an emission mitigation device.

In another aspect, the present disclosure provides a method for disinfecting a space in a building, the method comprising: monitor, by a controller comprising at least one processor and at least one memory having instructions stored thereon that are executable by the at least one processor, one or more conditions of the space; and selectively activate and deactivate, by the controller, at least one Far UV-C disinfection device installed in the space using the conditions of the space and one or more of an energy budget a target total operating cost, or a net emissions target, wherein the Far UV-C disinfection device comprises at least one Far UV-C light source structured to output disinfecting light at a wavelength between 200 nm and 230 nm.

In some embodiments, selectively activating and deactivating the at least one Far UV-C disinfection device comprises selectively activating and deactivating the at least one far UV-C disinfection device to not exceed one or more of the energy budget, the target total operating cost, or the net emissions target.

In some embodiments, selectively activating and deactivating the at least one Far UV-C disinfection device comprises selectively activating and deactivating the at least one far UV-C disinfection device to achieve a desired disinfection level and wherein selectively activating the at least one Far UV-C disinfection device can exceed one or more of the energy budget, the target total operating cost, or the net emissions target to achieve the desired disinfection level.

In some embodiments, the method further comprises determining a prevalence, a location, and a type for identified pathogens.

In some embodiments, an Equivalent Clean Airflow for infection mitigation of the Far UV-C disinfection device is stored in the controller.

In some embodiments, selectively activating and deactivating the at least one Far UV-C disinfection device comprises selectively activating and deactivating the at least one far UV-C disinfection device to meet an infection risk mitigation standard.

In some embodiments, a Far UV-C tracer is used to measure an effective disinfection provided by the Far UV-C disinfection device in the building space and wherein the effective disinfection provided by the Far UV-C disinfection device is stored in the controller.

In some embodiments, the controller periodically triggers a new Far UV-C tracer test to measure the effective disinfection provided by the Far UV-C disinfection device.

In some embodiments, the controller triggers a replacement of the one or more disinfection devices when the effective disinfection falls below a pre-determined threshold.

In some embodiments, the disinfection device further comprises an emission mitigation device.

In another aspect, the present disclosure provides one or more non-transitory computer readable media storing instructions thereon that, when executed by one or more processors, cause the one or more processors to perform operations comprising: monitoring one or more conditions of the space; and selectively activating and deactivating at least one Far UV-C disinfection device installed in the space using the conditions of the space and one or more of an energy budget, a target total operating cost, or a net emissions target, wherein the Far UV-C disinfection device comprises at least one Far UV-C light source structured to output disinfecting light at a wavelength between 200 nm and 230 nm.

DETAILED DESCRIPTION

Overview

A major goal of building management is to improve health outcomes for occupants in a building. Traditionally this has been accomplished using a combination of approaches, such as HVAC air circulation, air filtration, and air treatment. Some approaches have used UV spectrum light to treat air, resulting in pathogen inactivation. However such UV approaches are costly and have limited implementation options, because of the toxicity of UV exposure to humans at certain wavelengths and intensities.

Far UV-C lighting offers significant advantages over other disinfection means, particularly because building occupants can safely be exposed to Far UV-C at certain dosages. Thus, Far UV-C based methods and systems may be used to improve building health outcomes in occupied zones by continuously disinfecting ambient air and exposed surfaces. Such applications are of particular interest in buildings that are at elevated risk of pathogen transmission, such as hospitals and schools, and buildings that serve as transit points for large numbers of people, such as airports and train stations.

Building and HVAC System

Figure 1:
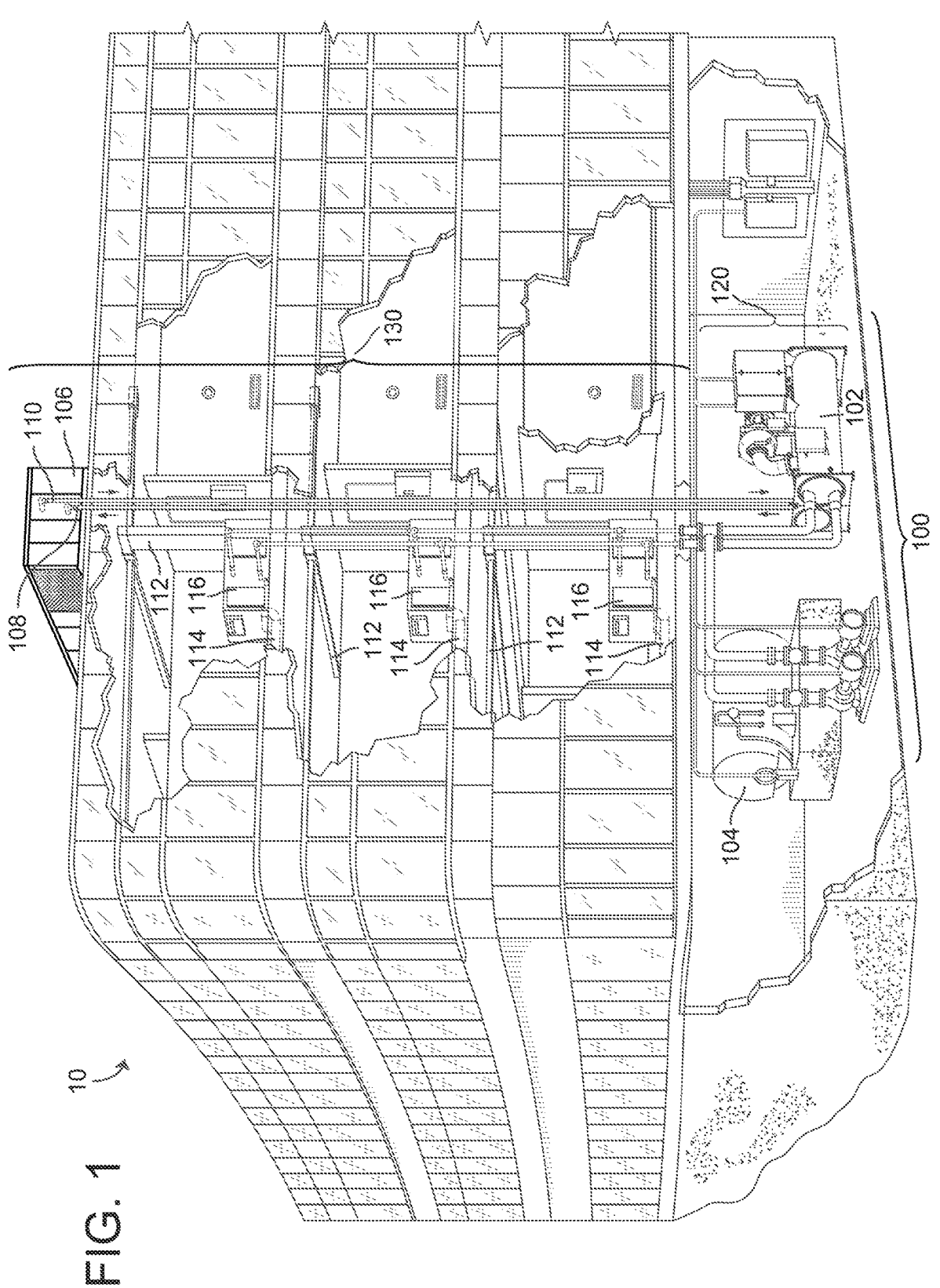
FIG. 1 is a drawing of a building equipped with a HVAC system, according to some embodiments.

Referring now to FIG. 1, a perspective view of a building 10 is shown. Building 10 can be served by a building management system (BMS). A BMS is, in general, a system of devices configured to control, monitor, and manage equipment in or around a building or building area. A BMS can include, for example, a HVAC system, a security system, a lighting system, a fire alerting system, a disinfection system, any other system that is capable of managing building functions or devices, or any combination thereof. An example of a BMS which can be used to monitor and control building 10 is described in U.S. patent application Ser. No. 14/717,593 filed May 20, 2015, the entire disclosure of which is incorporated by reference herein.

The BMS that serves building 10 may include a HVAC system 100. HVAC system 100 can include a plurality of HVAC devices (e.g., heaters, chillers, air handling units, pumps, fans, thermal energy storage, etc.) configured to provide heating, cooling, ventilation, or other services for building 10. For example, HVAC system 100 is shown to include a waterside system 120 and an airside system 130. Waterside system 120 may provide a heated or chilled fluid to an air handling unit of airside system 130. Airside system 130 may use the heated or chilled fluid to heat or cool an airflow provided to building 10. In some embodiments, waterside system 120 can be replaced with or supplemented by a central plant or central energy facility (described in greater detail with reference to FIG. 2). An example of an airside system which can be used in HVAC system 100 is described in greater detail with reference to FIG. 2.

HVAC system 100 is shown to include a chiller 102, a boiler 104, and a rooftop air handling unit (AHU) 106. Waterside system 120 may use boiler 104 and chiller 102 to heat or cool a working fluid (e.g., water, glycol, etc.) and may circulate the working fluid to AHU 106. In various embodiments, the HVAC devices of waterside system 120 can be located in or around building 10 (as shown in FIG. 1) or at an offsite location such as a central plant (e.g., a chiller plant, a steam plant, a heat plant, etc.). The working fluid can be heated in boiler 104 or cooled in chiller 102, depending on whether heating or cooling is required in building 10. Boiler 104 may add heat to the circulated fluid, for example, by burning a combustible material (e.g., natural gas) or using an electric heating element. Chiller 102 may place the circulated fluid in a heat exchange relationship with another fluid (e.g., a refrigerant) in a heat exchanger (e.g., an evaporator) to absorb heat from the circulated fluid. The working fluid from chiller 102 and/or boiler 104 can be transported to AHU 106 via piping 108.

AHU 106 may place the working fluid in a heat exchange relationship with an airflow passing through AHU 106 (e.g., via one or more stages of cooling coils and/or heating coils). The airflow can be, for example, outside air, return air from within building 10, or a combination of both. AHU 106 may transfer heat between the airflow and the working fluid to provide heating or cooling for the airflow. For example, AHU 106 can include one or more fans or blowers configured to pass the airflow over or through a heat exchanger containing the working fluid. The working fluid may then return to chiller 102 or boiler 104 via piping 110.

Airside system 130 may deliver the airflow supplied by AHU 106 (i.e., the supply airflow) to building 10 via air supply ducts 112 and may provide return air from building 10 to AHU 106 via air return ducts 114. In some embodiments, airside system 130 includes multiple variable air volume (VAV) units 116. For example, airside system 130 is shown to include a separate VAV unit 116 on each floor or zone of building 10. VAV units 116 can include dampers or other flow control elements that can be operated to control an amount of the supply airflow provided to individual zones of building 10. In other embodiments, airside system 130 delivers the supply airflow into one or more zones of building 10 (e.g., via supply ducts 112) without using intermediate VAV units 116 or other flow control elements. AHU 106 can include various sensors (e.g., temperature sensors, pressure sensors, etc.) configured to measure attributes of the supply airflow. AHU 106 may receive input from sensors located within AHU 106 and/or within the building zone and may adjust the flow rate, temperature, or other attributes of the supply airflow through AHU 106 to achieve setpoint conditions for the building zone.

Airside System

Figure 2:
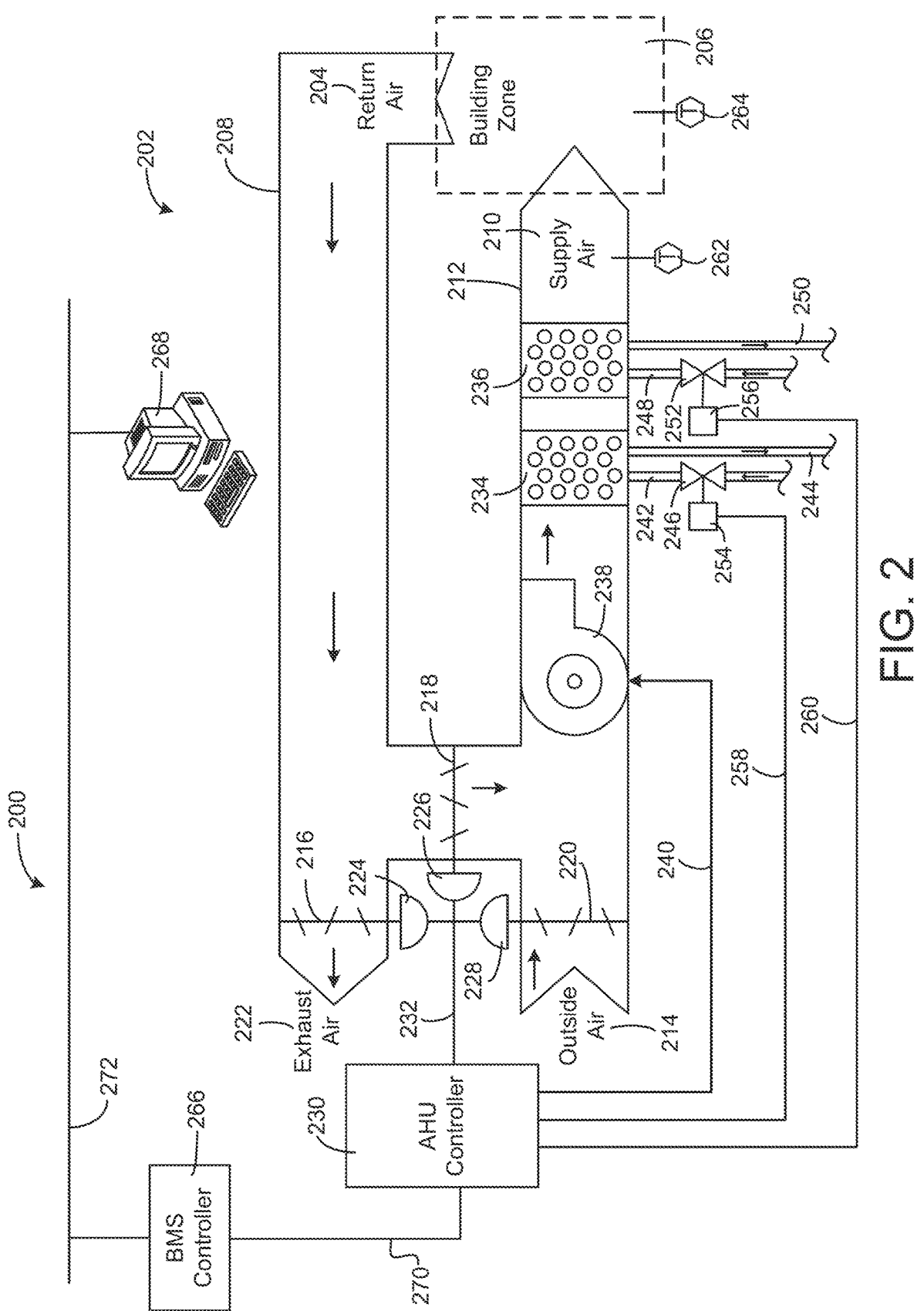
FIG. 2 is a block diagram of an airside system which can be implemented in the building of FIG. 1, according to some embodiments.

Referring now to FIG. 2, a block diagram of an airside system 200 is shown, according to some embodiments. In various embodiments, airside system 200 may supplement or replace airside system 130 in HVAC system 100 or can be implemented separate from HVAC system 100. When implemented in HVAC system 100, airside system 200 can include a subset of the HVAC devices in HVAC system 100 (e.g., AHU 106, VAV units 116, ducts 112-114, fans, dampers, etc.) and can be located in or around building 10. Airside system 200 may operate to heat, cool, humidify, dehumidify, filter, and/or disinfect an airflow provided to building 10 in some embodiments.

Airside system 200 is shown to include an economizer-type air handling unit (AHU) 202. Economizer-type AHUs vary the amount of outside air and return air used by the air handling unit for heating or cooling. For example, AHU 202 may receive return air 204 from building zone 206 via return air duct 208 and may deliver supply air 210 to building zone 206 via supply air duct 212. In some embodiments, AHU 202 is a rooftop unit located on the roof of building 10 (e.g., AHU 106 as shown in FIG. 1) or otherwise positioned to receive both return air 204 and outside air 214. AHU 202 can be configured to operate exhaust air damper 216, mixing damper 218, and outside air damper 220 to control an amount of outside air 214 and return air 204 that combine to form supply air 210. Any return air 204 that does not pass through mixing damper 218 can be exhausted from AHU 202 through exhaust damper 216 as exhaust air 222.

Each of dampers 216-220 can be operated by an actuator. For example, exhaust air damper 216 can be operated by actuator 224, mixing damper 218 can be operated by actuator 226, and outside air damper 220 can be operated by actuator 228. Actuators 224-228 may communicate with an AHU controller 230 via a communications link 232. Actuators 224-228 may receive control signals from AHU controller 230 and may provide feedback signals to AHU controller 230. Feedback signals can include, for example, an indication of a current actuator or damper position, an amount of torque or force exerted by the actuator, diagnostic information (e.g., results of diagnostic tests performed by actuators 224-228), status information, commissioning information, configuration settings, calibration data, and/or other types of information or data that can be collected, stored, or used by actuators 224-228. AHU controller 230 can be an economizer controller configured to use one or more control algorithms (e.g., state-based algorithms, extremum seeking control (ESC) algorithms, proportional-integral (PI) control algorithms, proportional-integral-derivative (PID) control algorithms, model predictive control (MPC) algorithms, feedback control algorithms, etc.) to control actuators 224-228.

Still referring to FIG. 2, AHU 202 is shown to include a cooling coil 234, a heating coil 236, and a fan 238 positioned within supply air duct 212. Fan 238 can be configured to force supply air 210 through cooling coil 234 and/or heating coil 236 and provide supply air 210 to building zone 206. AHU controller 230 may communicate with fan 238 via communications link 240 to control a flow rate of supply air 210. In some embodiments, AHU controller 230 controls an amount of heating or cooling applied to supply air 210 by modulating a speed of fan 238. In some embodiments, AHU 202 includes one or more air filters (e.g., filter 308) as described in greater detail with reference to FIG. 3. AHU controller 230 can be configured to control the disinfection device(s) 306 in different building zones 206 and route the airflow through the air filters to disinfect the airflow as described in greater detail below.

Cooling coil 234 may receive a chilled fluid from central plant 200 (e.g., from cold water loop 216) via piping 242 and may return the chilled fluid to central plant 200 via piping 244. Valve 246 can be positioned along piping 242 or piping 244 to control a flow rate of the chilled fluid through cooling coil 234. In some embodiments, cooling coil 234 includes multiple stages of cooling coils that can be independently activated and deactivated (e.g., by AHU controller 230, by BMS controller 266, etc.) to modulate an amount of cooling applied to supply air 210.

Heating coil 236 may receive a heated fluid from central plant 200 (e.g., from hot water loop 214) via piping 248 and may return the heated fluid to central plant 200 via piping 250. Valve 252 can be positioned along piping 248 or piping 250 to control a flow rate of the heated fluid through heating coil 236. In some embodiments, heating coil 236 includes multiple stages of heating coils that can be independently activated and deactivated (e.g., by AHU controller 230, by BMS controller 266, etc.) to modulate an amount of heating applied to supply air 210.

Each of valves 246 and 252 can be controlled by an actuator. For example, valve 246 can be controlled by actuator 254 and valve 252 can be controlled by actuator 256. Actuators 254-256 may communicate with AHU controller 230 via communications links 258-260. Actuators 254-256 may receive control signals from AHU controller 230 and may provide feedback signals to controller 230. In some embodiments, AHU controller 230 receives a measurement of the supply air temperature from a temperature sensor 262 positioned in supply air duct 212 (e.g., downstream of cooling coil 334 and/or heating coil 236). AHU controller 230 may also receive a measurement of the temperature of building zone 206 from a temperature sensor 264 located in building zone 206.

In some embodiments, AHU controller 230 operates valves 246 and 252 via actuators 254-256 to modulate an amount of heating or cooling provided to supply air 210 (e.g., to achieve a setpoint temperature for supply air 210 or to maintain the temperature of supply air 210 within a setpoint temperature range). The positions of valves 246 and 252 affect the amount of heating or cooling provided to supply air 210 by cooling coil 234 or heating coil 236 and may correlate with the amount of energy consumed to achieve a desired supply air temperature. AHU 230 may control the temperature of supply air 210 and/or building zone 206 by activating or deactivating coils 234-236, adjusting a speed of fan 238, or a combination of both.

Still referring to FIG. 2, airside system 200 is shown to include a building management system (BMS) controller 266 and a client device 268. BMS controller 266 can include one or more computer systems (e.g., servers, supervisory controllers, subsystem controllers, etc.) that serve as system level controllers, application or data servers, head nodes, or master controllers for airside system 200, central plant 200, HVAC system 100, and/or other controllable systems that serve building 10. BMS controller 266 may communicate with multiple downstream building systems or subsystems (e.g., HVAC system 100, a disinfection system, a security system, a lighting system, central plant 200, etc.) via a communications link 270 according to like or disparate protocols (e.g., LON, BACnet, etc.). In various embodiments, AHU controller 230 and BMS controller 266 can be separate (as shown in FIG. 2) or integrated. In an integrated implementation, AHU controller 230 can be a software module configured for execution by a processor of BMS controller 266.

In some embodiments, AHU controller 230 receives information from BMS controller 266 (e.g., commands, setpoints, operating boundaries, etc.) and provides information to BMS controller 266 (e.g., temperature measurements, valve or actuator positions, operating statuses, diagnostics, etc.). For example, AHU controller 230 may provide BMS controller 266 with temperature measurements from temperature sensors 262-264, equipment on/off states, equipment operating capacities, and/or any other information that can be used by BMS controller 266 to monitor or control a variable state or condition within building zone 206.

Client device 268 can include one or more human-machine interfaces or client interfaces (e.g., graphical user interfaces, reporting interfaces, text-based computer interfaces, client-facing web services, web servers that provide pages to web clients, etc.) for controlling, viewing, or otherwise interacting with HVAC system 100, its subsystems, and/or devices. Client device 268 can be a computer workstation, a client terminal, a remote or local interface, or any other type of user interface device. Client device 268 can be a stationary terminal or a mobile device. For example, client device 268 can be a desktop computer, a computer server with a user interface, a laptop computer, a tablet, a smartphone, a PDA, or any other type of mobile or non-mobile device. Client device 268 may communicate with BMS controller 266 and/or AHU controller 230 via communications link 272.

Disinfection System and Methods of Use

Overview

Figure 3:
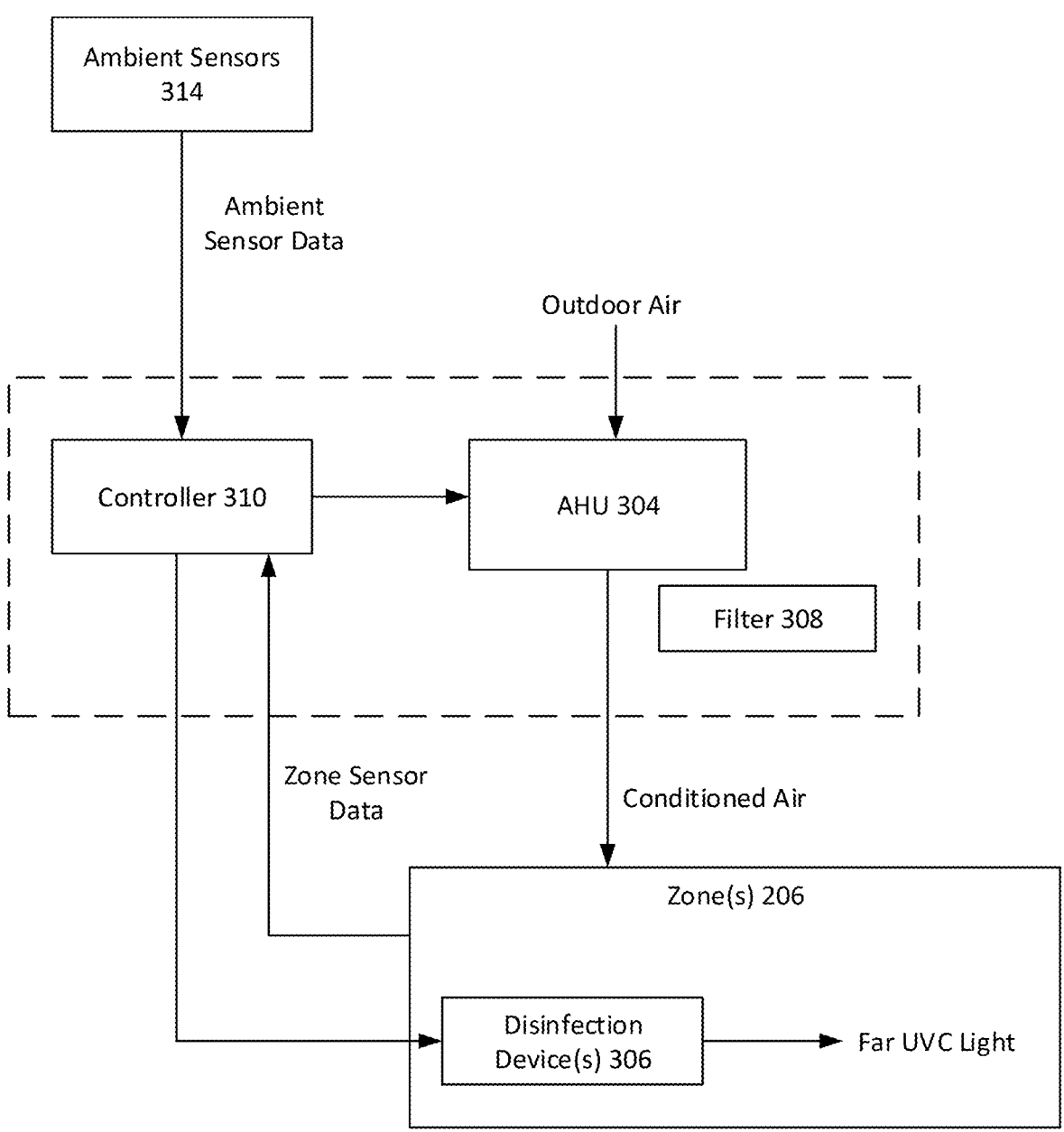
FIG. 3 is a block diagram of a disinfection system including a controller configured to operate disinfection device(s) and an air-handling unit (AHU) of the HVAC system of FIG. 1, according to some embodiments.

Referring now to FIG. 3, a block diagram of a disinfection system configured to inactivate pathogens in various zones of a building is shown and described, according to some embodiments. Disinfection systems can include an air handling unit (AHU) 304 (e.g., AHU 230, AHU 202, etc.) that can provide conditioned air (e.g., cooled air, supply air 210, etc.) to various building zones 206. The AHU 304 may draw air from the zones 206 in combination with drawing air from outside (e.g., outside air) to provide conditioned or clean air to zones 206. The disinfection system includes a controller 310 (e.g., AHU controller 230) that is configured to determine a fraction x of outdoor air to recirculated air that the AHU 304 should use to provide a desired amount of disinfection to building zones 206. In some embodiments, controller 310 can generate control signals for various dampers of AHU 304 so that AHU 304 operates to provide the conditioned air to building zones 206 using the fraction x.

The disinfection system can also include disinfection device(s) 306 located in various building zone(s) 206. The disinfection device(s) 306 can include Far UVC light(s) that are configured to provide disinfection as determined by controller 310 and/or based on user operating preferences. For example, the controller 310 can determine control signals for disinfection devices 306 emitting Far UVC light in combination with the fraction x of outdoor air to provide a desired amount of disinfection and satisfy an infection probability constraint. Disinfection devices can be optimized, designed, and applied as discussed in detail below.

The disinfection system can also include one or more filters 308 or filtration devices (e.g., air purifiers). In some embodiments, the filters 308 are configured to filter the conditioned air or recirculated air before it is provided to building zones 206 to provide a certain amount of disinfection. In this way, controller 310 can perform an optimization in real-time or as a planning tool to determine control signals for AHU 304 (e.g., the fraction x) and control signals for disinfection devices 306 (e.g., on/off commands or intensity variation commands) to provide disinfection for building zones 206 and reduce a probability of infection of individuals that are occupying building zones 206. Controller 310 can also function as a design tool that is configured to determine suggestions for building managers regarding benefits of installing or using filters 308 or disinfection devices 306, and/or specific benefits that may arise from using or installing a particular type or size of filter. Controller 310 can thereby facilitate informed design decisions to maintain sterilization of air that is provided to building zones 206 and reduce a likelihood of infection or spreading of infectious matter. The disinfection system can include multiple types of controllers, such as a centralized controller, a distributed controller, or an edge controller.

Wells-Riley Airborne Transmission

The systems and methods described herein may use an infection probability constraint in various optimizations (e.g., in on-line or real-time optimizations or in off-line optimizations) to facilitate reducing infection probability among residents or occupants of spaces that the HVAC system and the disinfection system serves. The infection probability constraint can be based on a steady-state Wells-Riley equation for a probability of airborne transmission of an infectious agent given by:

$$P := \frac{D}{S} = 1 - \exp\left(-\frac{Ipqt}{Q}\right)$$

where P is a probability that an individual becomes infected (e.g., in a zone, space, room, environment, etc.), D is a number of infected individuals (e.g., in the zone, space, room, environment, etc.), S is a total number of susceptible individuals (e.g., in the zone, space, room, environment, etc.), I is a number of infectious individuals (e.g., in the zone, space, room, environment, etc.), q is a disease quanta generation rate (e.g., with units of 1/sec), p is a volumetric breath rate of one individual (e.g., in), t is a total exposure time (e.g., in seconds), and Q is an outdoor ventilation rate (e.g., in). For example, Q may be a volumetric flow rate of fresh outdoor air that is provided to the building zones 206 by AHU 304.

When the Wells-Riley equation is implemented by controller 310 as described herein, controller 310 may use the Wells-Riley equation (or a dynamic version of the Wells-Riley equation) to determine an actual or current probability of infection P and operate the HVAC system 200 to maintain the actual probability of infection P below (or drive the actual probability of infection below) a constraint or maximum allowable value. The constraint value (e.g., $P_{MAX}$) may be a constant value, or may be adjustable by a user (e.g., a user-set value). For example, the user may set the constraint value of the probability of infection to a maximum desired probability of infection (e.g., either for on-line implementation of controller 310 to maintain the probability of infection below the maximum desired probability, or for an off-line implementation/simulation performed by controller 310 to determine various design parameters for HVAC system 200 such as filter size), or may select from various predetermined values (e.g., 3-5 different choices of the maximum desired probability of infection).

In some embodiments, the number of infectious individuals I can be determined by controller 310 based on data from the Centers for Disease and Control Prevention or a similar data source such as diagnosis data from a particular building 10 (e.g. a hospital). The value of I may be typically set equal to 1 but may vary as a function of occupancy of building zones 206.

The disease quanta generation rate q may be a function of the infectious agent. For example, more infectious diseases may have a higher value of q, while less infectious diseases may have a lower value of q. For example, the value of q for COVID-19 may be 30-300 (e.g., 100).

The value of the volumetric breath rate p may be based on a type of building space 206. For example, the volumetric breath rate p may be higher if the building zone 206 is a gym as opposed to an office setting. In general, an expected level of occupant activity may determine the value of the volumetric breath rate p.

A difference between D (the number of infected individuals) and I (the number of infectious individuals) is that D is a number of individuals who are infected (e.g., infected with a disease), while I is a number of people that are infected and are actively contagious (e.g., individuals that may spread the disease to other individuals or spread infectious particles when they exhale). The disease quanta generation rate indicates a number of infectious droplets that give a 63.2% chance of infecting an individual (e.g., 1−exp(−1)). For example, if an individual inhales k infectious particles, the probability that the individual becomes infected (P) is given by $$1 - \exp\left(-\frac{k}{k_0}\right)$$

where k is the number of infectious particles that the individual has inhaled, and $k_0$ is a quantum of particles for a particular disease (e.g., a predefined value for different diseases). The quanta generation rate q is the rate at which quanta are generated (e.g., $K/k_0$) where K is the rate of infectious particles exhaled by an infectious individual. It should be noted that values of the disease quanta generation rate q may be back-calculated from epidemiological data or may be tabulated for well-known diseases.

The Wells-Riley equation (shown above) is derived by assuming steady-state concentrations for infectious particles in the air. Assuming a well-mixed space:

$$V\frac{dN}{dt} = Iq - NQ$$

where V is a total air volume (e.g., in m³), N is a quantum concentration in the air, I is the number of infectious individuals, q is the disease quanta generation rate, and Q is the outdoor ventilation rate. The term Iq is quanta production by infectious individuals (e.g., as the individuals breathe out or exhale), and the term NQ is the quanta removal rate due to ventilation (e.g., due to operation of AHU 304).

Assuming steady-state conditions, the steady state quantum concentration in the air is expressed as:

$$N_{ss} = \frac{Iq}{Q}$$

according to some embodiments.

Therefore, if an individual inhales at an average rate of p (e.g., in m³/sec), over a period of length t the individual inhales a total volume pt or $N_{ss}ptk_0$ infectious particles. Therefore, based on a probability model used to define the quanta, the infectious probability is given by:

$$P = 1 - \exp\left(-\frac{k}{k_0}\right) = 1 - \exp(-N_{ss}pt) = 1 - \exp\left(-\frac{Iqpt}{Q}\right)$$

where P is the probability that an individual becomes infected, k is the number of infectious particles that the individual has inhaled, and $k_0$ is the quantum of particles for the particular disease.

Carbon Dioxide for Infectious Particles Proxy

While the above equations may rely on in-air infectious quanta concentration, measuring in-air infectious quanta concentration may be difficult. However, carbon dioxide ($CO2$) is a readily-measurable parameter that can be a proxy species, measured by zone sensors which return data to a controller 310. In some embodiments, a concentration of $CO2$ in the zones 206 may be directly related to a concentration of the infectious quanta.

A quantity $\phi$ that defines a ratio of an infected particle concentration in the building air to the infected particle concentration in the exhaled breath of an infectious individual is defined:

$$\phi := \frac{pN}{q}$$

where p is the volumetric breath rate for an individual, N is the quantum concentration in the air, and q is the disease quanta generation rate. Deriving the above equation with respect to time yields:

$$\frac{d\phi}{dt} = \frac{p}{q}\left(\frac{dN}{dt}\right) = \frac{Ip}{V} - \phi\left(\frac{Q}{V}\right)$$

where p is the volumetric breath rate for the individual, q is disease quanta generation rate, N is the quantum concentration in the air, t is time, I is the number of infectious individuals, V is the total air volume, $\phi$ is the ratio, and Q is the outdoor ventilation rate. Since it can be difficult to measure the ratio $\phi$ of the air, $CO2$ can be used as a proxy species.

Humans release $CO2$ when exhaling, which is ultimately transferred to the ambient sensors 314 via ventilation of an HVAC system. Therefore, the difference between $CO2$ particles and infectious particles is that all individuals (and not only the infectious population) release $CO2$ and that the outdoor air $CO2$ concentration is non-zero. However, it may be assumed that the ambient $CO2$ concentration is constant with respect to time, which implies that a new quantity C can be defined as the net indoor $CO2$ concentration (e.g., the indoor concentration minus the outdoor concentration). With this assumption, the following differential equation can be derived:

$$V\frac{dC}{dt} = Spc - QC$$

where V is the total air volume (e.g. in m³), C is the net indoor CO2 concentration, t is time, S is the total number of susceptible individuals (e.g., in building zone 206, or a modeled space, or all of building zones 206, or building 10), p is the volumetric breath rate for one individual, c is the net concentration of exhaled CO2, and Q is the outdoor ventilation rate. This equation assumes that the only way to remove infectious particles is with fresh air ventilation (e.g., by operating AHU 304 to draw outdoor air and use the outdoor air with recirculated air). A new quantity ψ can be defined that gives the ratio of net CO2 concentration in the building air to net CO2 concentration in the exhaled air:

$$\psi = \frac{C}{c}$$

where ψ is the ratio, C is the net indoor CO2 concentration, and c is the net concentration of exhaled CO2.

Deriving the ratio ψ with respect to time yields:

$$\frac{d\psi}{dt} = \frac{1}{c}\left(\frac{dC}{dt}\right) = \frac{Sp}{V} - \psi\left(\frac{Q}{V}\right)$$

according to some embodiments.

Combining the above equation with the quantity φ, it can be derived that:

$$\frac{d}{dt}\log\left(\frac{\phi}{\psi}\right) = \frac{1}{\phi}\left(\frac{d\phi}{dt}\right) - \frac{1}{\psi}\left(\frac{d\psi}{dt}\right) = \frac{p}{V}\left(\frac{1}{\phi} - \frac{S}{\psi}\right)$$

according to some embodiments. Assuming that the initial condition satisfies:

$$\phi(0) = \frac{1}{S}\psi(0)$$

it can be determined that the right-hand side of the $$\frac{d}{dt}\log\left(\frac{\phi}{\psi}\right)$$

equation becomes zero. This implies that the term log $$\left(\frac{\phi}{\psi}\right)$$

and therefore $$\frac{\phi}{\psi}$$

is a constant. Therefore, φ/ψ is constant for all times t and not merely initial conditions when t=0.

The $$\frac{d}{dt}\log\left(\frac{\phi}{\psi}\right)$$

relationship only holds true when fresh outdoor air is used as the only disinfection mechanism. However, in many cases HVAC system 200 may include one or more filters 308, and disinfection devices 306 that can be operated to provide disinfection for building zones 206. If additional infection mitigation strategies are used, the ventilation rate may instead by an effective ventilation rate for infectious quanta that is different than that of the CO2. Additionally, the only way for the initial conditions φ(0) and ψ(0) to be in proportion is for both to be zero. This assumption can be reasonable if HVAC system 200 operates over a prolonged time period (such as overnight, when the concentrations have sufficient time to reach equilibrium zero values). However, ventilation is often partially or completely disabled overnight and therefore the two quantities φ and ψ are not related. However, CO2 concentration can be measured to determine common model parameters (e.g., for the overall system volume V) without being used to estimate current infectious particle concentrations. If fresh outdoor air ventilation is the only mechanism for disinfection of zones 206, and the HVAC system 200 is run so that the concentrations reach equilibrium, CO2 concentration can be measured and used to estimate current infectious particle concentrations.

Dynamic Extension and Infection Probability Constraints

Referring still to FIG. 3, it may be desirable to model the infectious quanta concentration N of building zones 206 as a dynamic parameter rather than assuming N is equal to the steady state $N_{SS}$ value. For example, if infectious individuals enter building zones 206, leave building zones 206, etc., the infectious quanta concentration N may change over time. This can also be due to the fact that the effective fresh air ventilation rate (which includes outdoor air intake as well as filtration or Far UV-C disinfection that affects the infectious agent concentration in the supply air that is provided by AHU 304 to zones 206) can vary as HVAC system 200 operates.

Therefore, assuming that the infectious quanta concentration N(t) is a time-varying quantity, for a given time period t∈ [0, T], an individual breathes in:

$$k_{[0,T]} = \int_0^T pk_0 N(t)dt$$

where $k_{[0,T]}$ is the number of infectious particles that an individual inhales over the given time period [0, T], p is the volumetric breath rate of one individual, $k_0$ is the quantum of particles for a particular disease, and N(t) is the time-varying quantum concentration of the infectious particle in the air.

Since $$P = 1 - \exp\left(-\frac{k}{k_0}\right)$$

the above equation can be rearranged and substitution yields:

$$-\log(1 - P_{[0,T]}) = \int_0^T pN(t)dt \approx \Delta \sum_t pN_t$$

according to some embodiments.

Assuming an upper boundary $$P_{[0,T]}^{max}$$

on acceptable or desirable infection probability, a constraint is defined as:

$$\frac{\Delta}{T}\sum_t N_t \leq -\frac{1}{pT}\log(1 - P_{[0,T]})$$

according to some embodiments. The constraint can define a fixed upper boundary on an average value of $N_t$ over the given time interval.

Disinfection Devices and Optimization Thereof for a Building Space

The systems and methods disclosed herein may include disinfection device(s) 306 that include one or more Far UV-C lights. Far UV-C lights can emit light at one or more wavelengths (e.g., 222 nm, 207 nm, any wavelength inclusively within a range from 200 nm to 232 nm, etc.) or across multiple wavelengths within a range of wavelengths, including for example 200 nm to 232 nm, inclusively. In some implementations, the wavelength(s) emitted by the Far UV-C lights may be within about a 10 nm range above or below a target wavelength, such as 222 nm (e.g., from 212 nm to 232 nm, inclusively). Far UV-C lights can include any variety of bulb or emission source for Far UV-C light. In some embodiments, the amount and intensity of light emitted by the disinfection device 306 and the placement of the device is optimized for disinfection of a building zone 206 through a pathogen identification process and/or through a light simulation process. Pathogen identification can be accomplished using methods well known in the art, such as DNA sequencing or antibody-based detection method, and samples may be taken from surfaces or ambient air using known techniques. Light simulation can be accomplished using any known light simulation technique, such as a technique that allows for system optimization based on expected light coverage and objects that will block light coverage for a given area. In some embodiments, system optimization for a zone 206 will include varying the number of disinfection devices and/or Far UV-C lights, the placement of disinfection devices, and/or the intensity of the light emitted by the disinfection devices. In some embodiments, multiple disinfection devices 306 may be arranged in a building zone 206. In some embodiments, multiple disinfection devices 306 are arranged around light blocking objects, such as bathroom stalls or curtains, to ensure sufficient surface-Far UV-C exposure throughout a building zone 206. Disinfection devices 306 achieve pathogen inactivation by shining Far UV-C light onto said pathogens, whether in the air or on a surface. In some embodiments, disinfection devices 306 are situated in a building zone 206 to shine Far UV-C light at known potential pathogen sources, such as the head of a bed or the bowl of a toilet.

In some embodiments, the disinfection device 306 is laboratory tested using standard procedures for managing infectious aerosols, such as the ASHRAE 241 standard, the ASHRAE Standard 185.3P, or the AHAM Standard AC-5. Test results for a disinfection device 306 can be expressed in Equivalent Clean Airflow for infection mitigation (ECAi) as expressed in airflow units (e.g. CFM or L/s). For example, a 15-watt disinfection device 306 could be rated with an ECAi of 100 CFM. In some embodiments, the ECAi for a disinfection device 306 operated at varying levels of power and/or light output can be measured and stored in the building system, optionally in a controller 310 (e.g., low power/output=30 CFM, medium power/output=60 CFM, high power/output=100 CFM). The building management system can use the disinfection device 306 ECAi values to operate one or more disinfection devices 306 to achieve a desired ECAi in different building zones. The minimum ECAi requirements per person to sufficiently mitigate infection risk, as described by ASHRAE 241 or an equivalent standard, can be stored in the building management system, optionally in a controller 310, such that the system can vary disinfection device 306 activation and/or light output to meet the ASHRAE 241 standards. ASHRAE 241 standards apply to buildings when in Infection Risk Management Mode (IRMM). The building management system could be configured to turn one or more disinfection devices 306 off when the building is not in IRMM or to operate the disinfection devices, and other systems, to achieve varying levels of IRMM (e.g. 50%, 55%, 65%, 70%, 75%, 80%, 85%, 90%, 95%, 100%, 105%, 110%, 115%, 120%, 125%, 150%, 175%, or 200% IRMM). The building management system can assess the ASHRAE 241 standard requirements for different types of building zones based on zone type and occupancy levels, which can be determined using occupancy sensors or CO2 sensors as described herein. The building management system can also measure the ECAi provided by all non-disinfection devices. Using ECAi from non-disinfection devices, the building management system can selectively activate or deactivate one or more disinfection devices 306 or vary light output levels thereof to achieve the ECAi required by the ASHRAE 241 standards, or an equivalent thereof, while minimizing disinfection device 306 activity and power consumption.

Disinfection Device Design

The disinfection devices of the present disclosure include independent and integrated designs. Independent designs may be incorporated into a building zone 206 independent of other building components. For example, in some embodiments, independent designs include installation of a disinfection device 306 on a ceiling, wall, or floor as its own fixture. Integrated designs may be incorporated into a building space using another building fixture. For example, in some embodiments, integrated designs include installation of a disinfection device 306 as part of a visible lighting fixture, a carbon monoxide detector, a smoke detector, and/or sensors associated with a fire safety system.

The systems and methods of the present disclosure can be powered through connection to an external source and/or through internal means. In some embodiments, a disinfection device 306 is powered through integration with another building component that includes a power source, such as a visible lighting fixture, a carbon monoxide detector, or a smoke detector. In some embodiments, a disinfection device 306 is powered through integration into a building power system or a building Ethernet system (e.g., a power over Ethernet (POE) system). In some embodiments, a disinfection device 306 is powered through a battery. In some embodiments, a disinfection device includes a battery backup power source.

In some embodiments the activity of a disinfection device 306 is optimized to reduce energy consumption, total operating costs, environmental impact, or a combination thereof. For example, each disinfection device 306 can report power draw measurements to the building management system on a regular basis (e.g. hourly, daily, or weekly), which information can be stored in the building management system, optionally in a controller 310. The building management system can use an energy budget for a given period of time (e.g. hourly, daily, weekly) to selectively activate and deactivate one or more disinfection devices 306 or other building systems. The energy consumption measurements can be combined with measurements of run hours for the disinfection device 306 to create a total operating cost assessment, with run hours used to calculate estimated disinfection device replacement timing and costs. The total operating cost assessment can be stored in the building management system, optionally in a controller 310, and the building management system can use the total operating cost assessment to selectively activate and deactivate one or more disinfection devices 306. The building system can use a net emissions target to selectively activate and deactivate one or more disinfection devices. The disinfection device 306 energy consumption measurements over a period of time can be used to estimate carbon emissions from the energy consumed during that period. The estimated replacement of disinfection devices 306 based on run time over a given period can be used to estimate the carbon emissions from creating new disinfection devices. The building management system can use the estimated carbon emissions from energy consumption and disinfection device replacement to calculate the net emissions of one or more disinfection devices 306. The building management system can be configured to use the energy budget, the target total operating cost, the net emissions target, or a combination thereof to selectively activate and deactivate one or more disinfection devices 306. In some embodiments, the building management system selectively activates and deactivates one or more disinfection devices 306 to not exceed the energy budget, the target total operating cost, or the net emissions target. In other embodiments the building management system selectively activates and deactivates one or more disinfection devices 306 to achieve a desired disinfection level and one or more of the energy budget, the target total operating cost, or the net emissions target can be exceeded to achieve the desired disinfection level. In some embodiments, a controller 310 selectively activates and deactivates a disinfection device 306 or varies light output from a disinfection device 306 to not exceed the energy budget, the target total operating cost, or the net emissions target. In other embodiments, a controller 310 selectively activates and deactivates a disinfection device 306 or varies light output from a disinfection device 306 to achieve a desired disinfection levels and can exceed one or more of the energy budget, the target total operating cost, or the net emissions target to achieve the desired disinfection level. In some embodiments, the desired disinfection level will require varying amounts of Far UV-C light depending on the type, abundance, and location of pathogens in a building zone. For example, inactivation of viruses typically requires less UV-C light than inactivation of bacteria. Accordingly, in some embodiments the desired disinfection level will require more Far UV-C light because of the pathogen type, and in some embodiments the desired disinfection level will require less Far UV-C light because of pathogen type. In some embodiments, the building system will selectively activate and deactivate one or more disinfection devices to achieve an increased level of IRMM (e.g. 105%, 110%, 115%, 120%, 125%, 150%, 175%, or 200% IRMM) based on pathogen type. In some embodiments, the building system will selectively activate and deactivate one or more disinfection devices to achieve a decreased level of IRMM (e.g., 50%, 55%, 65%, 70%, 75%, 80%, 85%, 90%, or 95% IRMM) based on pathogen type.

The disinfection devices of the present disclosure may be of a modular design, such that consumable components can be replaced and additional elements can be added without replacing an entire device, which reduces the net environmental impact of using and operating the disinfection devices of the present disclosure. For example, a modular design allows for the replacement of a spent Far UV-C light bulb without replacing the entire disinfection device 306. By using a modular design, elements such as sensors can be added to a disinfection device to provide a new functionality or optimize the device for a given building zone 206. For example, additional Far UV-C light sources can be added to a disinfection device 306 to optimize the device for use in a particular building zone 206 which requires greater amounts of Far UV-C light to achieve pathogen inactivation. In order to minimize costs and maximize light lifetime while maintaining disinfection, Far UV-C lighting can be applied to a building zone 206 only when it is occupied. In some embodiments, a disinfection device 306 also includes a carbon dioxide sensor, configured to return data to a controller 310. In some embodiments, the controller 310 activates the disinfection device 306 once carbon dioxide levels rise above a pre-determined threshold value, indicating space occupancy (or occupancy at a certain level) and the potential presence of pathogens emitted by occupants, as described above. In some embodiments, the disinfection device 306 includes an edge controller that activates the disinfection device based on input from sensors in the device. In some embodiments, the disinfection device 306 includes a people counting sensor to determine occupancy (e.g., an occupancy sensor configured to sense how many occupants (e.g., people) are in a space).

In some embodiments, the disinfection device 306 may be controlled (e.g., via the controller 310 and/or a controller of the disinfection device 306) based on one or more of various direct or indirect indications of occupancy and/or presence of pathogens. In some such implementations, the disinfection device 306 may be activated and/or deactivated responsive to a combination of multiple factors. For example, the disinfection device could be activated and/or deactivated based on a combination of carbon dioxide readings and ventilation rate in the space. Carbon dioxide readings are a measure of ventilation per person. Accordingly, low carbon dioxide readings could mean that occupancy in the space is low, or they could mean that the airside system (e.g., air handling unit) is moving air through the space (replacing air in the space with outside, or clean, air) at a high rate. In some such implementations, the disinfection device 306 may be activated and/or deactivated responsive to both carbon dioxide data and ventilation rate data to account for variations in ventilation rate and help ensure that the carbon dioxide readings upon which the disinfection device 306 is controlled are based on occupancy of the space.

Pathogen inactivation upon exposure to Far UV-C lighting is not immediate, and therefore a disinfection device 306 may need to continue to operate after a space is no longer occupied to ensure that disinfection is achieved. In some embodiments, the controller 310 continues to operate a disinfection device 306 for a pre-determined amount of time after a room is no longer occupied, or occupancy drops below a particular level (e.g., responsive to sensed carbon dioxide dropping below a particular predetermined level, which may be the same or different than a level at which the disinfection device 306 is activated). In some embodiments, a light intensity sensor and/or a power consumption sensor can be added to the modular design of the disinfection device 306. In some embodiments, a building management system receives data from the light intensity sensor and uses it to determine whether the space is occupied and controls activation and deactivation of the disinfection device 306 based on the detected occupancy (e.g., deactivating the device when the space is unoccupied, activating the device for a certain amount of time after the space becomes unoccupied and then deactivating the device, etc.). In some embodiments, the building management system may use a power consumption sensor that measures power consumption of devices in the space, such as the lighting in the space, to sense or estimate occupancy and control the disinfection device 306 in a similar fashion. In some embodiments, the building management system can increase or decrease the light intensity from a disinfection device in a given space to maintain and/or change disinfection as conditions, such as occupancy, change. In some embodiments a building control system can use the power consumption sensor to determine power draw by a disinfection device and take one or more actions, such as ensure the disinfection device is functioning, modifying or monitoring functioning of the device to limit energy consumption in different conditions, etc.

In some implementations, the disinfection device 306 may be controlled based in part on characteristics or preferences of a user or occupant of a space. For example, in some implementations (e.g., in a healthcare/hospital setting), the disinfection device 306 may be controlled based in part on a medical status of a patient who is occupying or scheduled to be occupying a space. In some such implementations, for a patient who is immunocompromised and is scheduled to enter a room, the disinfection device 306 may be activated to disinfect the room before the patient enters and disabled while the patient is in the space. In one example, if a patient is in surgery and scheduled to go to room 201 after surgery, the disinfection device 306 in room 201 may be run for two hours prior to occupancy (e.g., regardless of whether there are other occupants during that time) but, optionally, disabled when the patient arrives or is scheduled to arrive after surgery. It should be understood that the present disclosure is not limited to such an example and encompasses modifying operation of disinfection device 306 responsive to any sort of user/occupant condition, characteristic, and/or preference.

The systems and methods of the present disclosure may include a controller 310 for varying light intensity from a disinfection device 306. In some embodiments, the controller 310 increases light intensity based on pathogen prevalence data. Pathogen prevalence and identification can be accomplished using methods well known in the art, such as DNA sequencing or antibody-based detection methods. Some buildings, such as hospitals or nursing homes, routinely test samples for pathogens, and such data can be used to determine pathogen prevalence in some embodiments. Data on pathogen prevalence from the CDC or other public health organizations can also be used in certain embodiments. Continuous pathogen prevalence data, obtained from a sensor placed in one or more spaces or zones of the building and configured to continuously or semi-continuously (e.g., periodically) monitor for presence of a pathogen, can also be used by the controller in some embodiments. In some embodiments, sensors that measure for presence of pathogens at discrete times or based on certain conditions should be used. It should be understood that the features of the present disclosure could be used in conjunction with any type of sensor or method of sensing or estimating/predicting presence of a pathogen or other substance in a space of a building, and the present disclosure is not limited to any particular sensor/device or method. Pathogen prevalence data is useful for ensuring optimal pathogen inactivation while minimizing associated costs. For example, because viruses require less Far UV-C light to achieve inactivation than bacteria, a controller can decrease light intensity in a space wherein viruses are present but bacterial pathogens are not and/or can decrease an amount of time the Far UV-C light is active (e.g., in embodiments where the Far UV-C lighting system is not capable of varying intensities). In some embodiments, a controller 310 can vary Far UV-C output from a disinfection device 306 based on a diagnosis of a particular disease. For example, if a patient in a room is diagnosed with a virus, the controller can vary light intensity to achieve viral inactivation while minimizing costs. As used herein, it should be understood that varying disinfecting light output can mean varying intensity of one or more disinfecting devices, varying a number of activated disinfecting devices and/or elements of disinfecting devices, varying an on and off time (e.g., via pulse width modulation) of the disinfecting devices, and/or using any other method that increases or decreases an amount of disinfecting light to which the space or a portion thereof is exposed and/or an amount of time during which the space or a portion thereof is exposed.

Some technical solutions of the present application include a disinfection device 306 having a light source that emits Far UV-C light and an emission mitigation device that reduces emissions that may be associated with Far UV-C light. See U.S. 63/537,999 for a discussion of emissions removal and Far UV-C lighting. The emission mitigation device may be disposed within the disinfection device 306. The emission mitigation device may be isolated and/or separated from an external portion of the disinfection device 306. For example, the emission mitigation device may be enclosed within a body of the disinfection device 306. Emissions emitted by the disinfection device 306 may be collected within the body of the disinfection device 306. In some embodiments, the disinfection device comprises an emissions sensor, optionally an ozone sensor. The emissions sensor may be disposed within the disinfection device 306. The emissions sensor may be isolated and/or separated from an external portion of the disinfection device 306. For example, the emissions sensor may be enclosed within a body of the disinfection device 306. The emissions sensor can report emissions information to the building management system on a constant or periodic (e.g. by the minute, hourly, daily, weekly, etc.) basis. The building management system can use the emissions information to selectively activate and deactivate one or more disinfection devices, and/or other building systems, to remain below a predetermined emissions threshold. In some embodiments, the emissions sensor is an ozone sensor. In some embodiments, the pre-determined emissions threshold is an ozone threshold (e.g., an ozone threshold of no greater than 5 parts per million).

Emissions collected within the body of the disinfection device 306 may be exposed to the emission mitigation device which may result in a reduction in an amount of the emission. For example, ozone may be collected within the body and the emission mitigation device may emit light including a wavelength that breaks down ozone (e.g., an emission). The emission mitigation device breaking down ozone may reduce an amount of ozone.

As another example, the emission mitigation device may include chemical elements and the chemical elements may collect and/or capture portions of the amount of emissions emitted by the disinfection device 306. To continue this example, the chemical elements may include activated carbon and the activated carbon may capture at least a portion of the amount of emissions (e.g., ozone) to reduce the amount of emissions emitted by the disinfection device 306. In some embodiments, the emission mitigation device may include one or more components and/or elements to reduce the amount of emissions emitted by the disinfection device 306. For example, the emission mitigation device may include a light source and chemical elements.

Disinfection Device Applications and Function Verification

The systems and methods of the present disclosure can make use of occupant location information to identify risks for cross-contamination between building zones 206, and optimize disinfection accordingly. For example, individuals identification (ID) badges can provide the location of individuals as they move throughout a building 10, and a building management system can identify any individuals who have passed through zones 206 that may have pathogens present in the air or surface. Such individuals can then be notified of the need to enter a zone 206 with Far UV-C application for a pre-determined period of time, thus achieving disinfection. Data such as the aforementioned data may be helpful in determining risk levels associated with different areas of a building (e.g., higher-risk areas where individuals from multiple different areas cross paths and/or interact, and where spread of infectious particles may be more likely). In some implementations, the data discussed herein may be used to help determine where to place disinfection devices (e.g., to place or focus disinfection devices, such as by putting more disinfection devices, in higher-risk locations). In some implementations, the data may additionally or alternatively be used in operation to determine when to turn disinfection devices on or off, an intensity of the output of the disinfection devices, etc. In some such implementations, the system may balance energy usage and infection control by activating more devices, at higher intensity, and/or for more time in higher risk areas and activating less devices, at lower intensity, and/or for less time in lower risk areas.

The systems and methods of the present disclosure include the creation of a Far UV-C air lock. The air lock is created by surrounding infectious or sensitive areas of a building with volumes of air that are continuously disinfected by the systems and methods of the present disclosure. For example, in some embodiments the air lock is created by placing disinfection devices at every entrance to a building zone 206, such as an infectious disease ward, wherein the disinfection devices are configured to operate in the entrances and are in continuous operation to achieve constant pathogen inactivation in a given volume of air.

The systems and methods of the present disclosure include light verification methods to ensure sufficient Far UV-C output from disinfection devices 306. Light output from the disinfection devices 306 may be optimized using light simulation models, as discussed previously. To confirm that systems are operating as expected, methods of the present disclosure include light intensity verification. In some embodiments, light intensity verification is achieved via passive or manual systems. In some embodiments, a light intensity sensor is integrated into a space, for example by being mounted on a wall, to constantly provide feedback to a building management system on actual Far UV-C intensity in the building zone 206. In some embodiments, a Far UV-C dose card that changes color over time based on Far UV-C exposure can be placed in a space for a set period of time to verify Far UV-C output. Such a dose card can be placed on a surface of interest, such as a hospital bed or school desk. In some embodiments, dosage card data is recorded manually and entered into a building management system. In other embodiments, a building management system continuously monitors the dosage cards. For example, dosage cards can be monitored by cameras and data on color change over time generated using video analytics can be provided to a building management system. In some embodiments, a light intensity sensor is brought into a space, data is recorded, and that data is then provided to a building management system. In some embodiments, light intensity sensors can be independent devices or can be integrated into an existing device, such as a smart phone, an ID badge, or a shared piece of equipment that regularly moves throughout a building (e.g., an IV cart in a hospital or a movable whiteboard in a school). A light intensity sensor integrated into an ID badge can be a Far UV-C dosage card, and can verify Far UV-C light intensity and exposure for an individual as they move throughout a building. ID badge integration is useful for determining total Far UV-C exposure to individuals, which allows for system modification to prevent over-exposure. Light intensity verification can be done continuously or at a regular interval, for example once every three months. In some embodiments a UV-C sensitive tracer is used to measure the effective disinfection provided by a disinfection device 306 in a building zone, optionally via the use of a test pathogen that is tagged or marked for identification. In some embodiments, the building zone UV-C tracer data is compared with laboratory disinfection test values from the Far UV-C disinfection device. In some embodiments, the UVC tracer measurements are stored the building management system, optionally in a controller 310, and the building management system can use the UVC tracer measurements to optimize disinfection in a building zone. In some embodiments, the building management system will periodically trigger a new UVC tracer test for a disinfection device to generate updated results, wherein the updated UVC tracer data is stored in the building management system, optionally in a controller 310. In some embodiments, the controller is configured to use the effective disinfection of the one or more disinfection devices to trigger a replacement of the one or more disinfection devices when the effective disinfection falls below a pre-determined threshold.

The systems and methods of the present disclosure include disinfection confirmation testing, which can be performed regularly or on a case by case basis. In some embodiments, disinfection confirmation is achieved by releasing a detection component into a space with a disinfection device, collecting samples form surfaces and air, operating the disinfection device, and then collecting more surface and air samples. The detection component can be a known virus or bacteria that is non-pathogenic, such as, for example, a bacteriophage. In such an embodiment, disinfection confirmation is established by a result showing that the known virus or bacteria was not inactivated before disinfection device operation, but was inactivated after disinfection device operation. Alternatively, the detection component can be a Far UV-C reactive compound. In such an embodiment, disinfection confirmation is established by a result showing that after disinfection device operation the Far UV-C reactive compound was altered by Far UV-C light exposure.

Anticipated Environmental Applications

The systems and methods of the present disclosure are suitable for application in a number of environments. For example, the disclosed systems and methods can be applied in a transportation context, such as on a bus, boat, or plane or in a bus terminal, port, or airport, to minimize the transmission of pathogens on such routes. In other embodiments, the disclosed systems and methods can be used in waiting rooms to minimize the disease risk to employees and customers/patients. In other embodiments, the disclosed systems and methods are applied on military bases, including in communal areas, to minimize the spread of disease and protect against bioweapons. In still other embodiments, the disclosed systems and methods are applied using portable installations, which are suitable for use during travel or at an emergency site, such as a natural disaster. In other embodiments, the disclosed systems and methods are applied to minimize disease risk among children, for example via application at schools or daycares. A person with skill in the art will recognize the many possible environments wherein the systems and methods of the present disclosure would be an appropriate and advantageous means to improve building health in occupied spaces.

Configuration of Exemplary Embodiments

Although the embodiments described herein include a specific order of method steps, the order of the steps may differ from what is described. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, calculation steps, processing steps, comparison steps, and decision steps.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

As used herein, the terms "circuit" or "controller" may include hardware structured to execute the functions described herein. In some embodiments, each respective "circuit" or "controller" may include machine-readable media for configuring the hardware to execute the functions described herein. The circuit or controller may be embodied as one or more circuitry components including, but not limited to, processing circuitry, network interfaces, peripheral devices, input devices, output devices, sensors, etc. In some embodiments, a circuit or controller may take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" or "controller" may include any type of component for accomplishing or facilitating achievement of the operations described herein. For example, a circuit or controller as described herein may include one or more transistors, logic gates (e.g., NAND, AND, NOR, OR, XOR, NOT, XNOR, etc.), resistors, multiplexers, registers, capacitors, inductors, diodes, wiring, and so on).

The "circuit" or "controller" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits or controllers (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit, controller, or components thereof may be disposed locally (e.g., as part of a local server, a local computing system, etc.) or remotely (e.g., as part of a remote server such as a cloud based server). To that end, a "circuit" or "controller" as described herein may include components that are distributed across one or more locations.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

What is claimed is:

1. A disinfection device system of a building comprising:
a controller comprising at least one processor and at least one memory having instructions stored thereon that, when executed by the at least one processor, are configured to cause the at least one processor to:
monitor one or more conditions of a space in the building; and
selectively activate and deactivate at least one Far UV-C disinfection device installed in the space using the conditions of the space and one or more of an energy budget, a target total operating cost, or a net emissions target, wherein the Far UV-C disinfection device comprises at least one Far UV-C light source structured to output disinfecting light at a wavelength between 200 nm and 230 nm.

2. The system of claim 1, wherein the at least one processor is configured to selectively activate and deactivate the at least one Far UV-C disinfection device to not exceed one or more of the energy budget, the target total operating cost, or the net emissions target.

3. The system of claim 1, wherein the at least one processor is configured to selectively activate and deactivate the at least one Far UV-C disinfection device to achieve a desired disinfection level, and wherein the at least one processor is configured to allow Far UV-C disinfection device activation to exceed one or more of the energy budget, the target total operating cost, or the net emissions target to achieve the desired disinfection level.

4. The system of claim 1, wherein an Equivalent Clean Airflow for infection mitigation of the Far UV-C disinfection device is stored in the controller.

5. The system of claim 4, wherein the controller selectively activates and deactivates the Far UV-C disinfection device to meet an infection risk mitigation standard.

6. The system of claim 1, further comprising a Far UV-C tracer, wherein the Far UV-C tracer is used to measure an effective disinfection provided by the Far UV-C disinfection device in the building and the effective disinfection is stored in the controller.

7. The system of claim 6, wherein the controller periodically triggers a new Far UV-C tracer test to measure the effective disinfection provided by the Far UV-C disinfection device.

8. The system of claim 6, wherein the controller is configured to use the effective disinfection of the one or more disinfection devices to trigger a replacement of the one or more disinfection devices when the effective disinfection falls below a pre-determined threshold.

9. The system of claim 1, wherein the disinfection device further comprises an emission mitigation device.

10. A method for disinfecting a space in a building, the method comprising:
monitor, by a controller comprising at least one processor and at least one memory having instructions stored thereon that are executable by the at least one processor, one or more conditions of the space; and
selectively activate and deactivate, by the controller, at least one Far UV-C disinfection device installed in the space using the conditions of the space and one or more of an energy budget a target total operating cost, or a net emissions target, wherein the Far UV-C disinfection device comprises at least one Far UV-C light source structured to output disinfecting light at a wavelength between 200 nm and 230 nm.

11. The method of claim 10, wherein selectively activating and deactivating the at least one Far UV-C disinfection device comprises selectively activating and deactivating the at least one far UV-C disinfection device to not exceed one or more of the energy budget, the target total operating cost, or the net emissions target.

12. The method of claim 10, wherein selectively activating and deactivating the at least one Far UV-C disinfection device comprises selectively activating and deactivating the at least one far UV-C disinfection device to achieve a desired disinfection level and wherein selectively activating the at least one Far UV-C disinfection device can exceed one or more of the energy budget, the target total operating cost, or the net emissions target to achieve the desired disinfection level.

13. The method of claim 10, further comprising determining a prevalence, a location, and a type for identified pathogens.

14. The method of claim 10, wherein an Equivalent Clean Airflow for infection mitigation of the Far UV-C disinfection device is stored in the controller.

15. The method of claim 14, wherein selectively activating and deactivating the at least one Far UV-C disinfection device comprises selectively activating and deactivating the at least one far UV-C disinfection device to meet an infection risk mitigation standard.

16. The method of claim 10, wherein a Far UV-C tracer is used to measure an effective disinfection provided by the Far UV-C disinfection device in the building space and wherein the effective disinfection provided by the Far UV-C disinfection device is stored in the controller.

17. The method of claim 16, wherein the controller periodically triggers a new Far UV-C tracer test to measure the effective disinfection provided by the Far UV-C disinfection device.

18. The method of claim 16, wherein the controller triggers a replacement of the one or more disinfection devices when the effective disinfection falls below a pre-determined threshold.

19. The method of claim 10, wherein the disinfection device further comprises an emission mitigation device.

20. One or more non-transitory computer readable media storing instructions thereon that, when executed by one or more processors, cause the one or more processors to perform operations comprising:
monitoring one or more conditions of the space; and
selectively activating and deactivating at least one Far UV-C disinfection device installed in the space using the conditions of the space and one or more of an energy budget, a target total operating cost, or a net emissions target, wherein the Far UV-C disinfection device comprises at least one Far UV-C light source structured to output disinfecting light at a wavelength between 200 nm and 230 nm.

* * * * *